(12) United States Patent
Bouchara et al.

(10) Patent No.: US 8,671,956 B2
(45) Date of Patent: Mar. 18, 2014

(54) METHOD FOR PERMANENT RESHAPING AND IN PARTICULAR FOR STRAIGHTENING, COMPRISING A STAGE OF STRAIGHTENING KERATINOUS FIBRES EMPLOYING A COMPOSITION COMPRISING AT LEAST 40% BY WEIGHT OF NON-SILICONE FATTY SUBSTANCES

(75) Inventors: Anne Bouchara, Paris (FR); Gaëlle Petit, Paris (FR); Frédéric Guerin, Paris (FR); Grégory Plos, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/993,411

(22) PCT Filed: Dec. 13, 2011

(86) PCT No.: PCT/EP2011/072585
§ 371 (c)(1),
(2), (4) Date: Aug. 7, 2013

(87) PCT Pub. No.: WO2012/080231
PCT Pub. Date: Jun. 21, 2012

(65) Prior Publication Data
US 2013/0306097 A1 Nov. 21, 2013

Related U.S. Application Data

(60) Provisional application No. 61/434,066, filed on Jan. 19, 2011.

(30) Foreign Application Priority Data

Dec. 14, 2010 (FR) ........................... 10 60505

(51) Int. Cl.
*A61Q 5/04* (2006.01)
*A45D 7/02* (2006.01)

(52) U.S. Cl.
USPC ............................. 132/202; 132/204

(58) Field of Classification Search
USPC ................................. 132/202, 204
See application file for complete search history.

(56) References Cited

U.S. PATENT DOCUMENTS

| | | | |
|---|---|---|---|
| 4,137,180 A | 1/1979 | Naik et al. | |
| 4,874,554 A | 10/1989 | Lange et al. | |
| 5,046,516 A | 9/1991 | Barradas | |
| 5,618,523 A | 4/1997 | Zysman et al. | |
| 5,773,611 A | 6/1998 | Zysman et al. | |
| 5,957,140 A | 9/1999 | McGee | |
| 2005/0013786 A1 | 1/2005 | Sabbach et al. | |
| 2010/0300472 A1* | 12/2010 | Malle et al. | 132/204 |

FOREIGN PATENT DOCUMENTS

| | | |
|---|---|---|
| EP | 1 468 667 | 10/2004 |
| FR | 2 673 179 | 8/1992 |
| WO | 2007/135298 | 11/2007 |
| WO | 2008/156459 | 12/2008 |

OTHER PUBLICATIONS

Database GNPD [Online] Mintel; Ultimate Salon Profesionals: "Intensive Hair & Skin Treatment Oil—Enjoy," XP002657280, Database accession No. 1385801, Aug. 2010.
Database GNPD [Online] Mintel; M.S. Rio Industria e Comercio de Cosmeticos: "Flat Iron Serum—Gllendex Natural Lise System," XP002657281, Database accession No. 1134090, Jul. 2010.
Florence, Nicholas, "The Use of Hyperbranched Polyalphaolefins in Hair Care Formulations," IP.COM Journal, IP.COM Inc., West Henrietta, NY, US, XP13132519, ISSN: 1533-0001, Jun. 25, 2009.
International Search Report for PCT/EP2011/072585.
Porter, M.R., "Handbook of Surfactants," published by Blackie & Son, 1991, pp. 116-178.
Downing in Arch. Dermatol, vol. 123, 1987, pp. 1381-1384.

* cited by examiner

*Primary Examiner* — Eisa Elhilo
(74) *Attorney, Agent, or Firm* — O'Brien Jones, PLLC

(57) ABSTRACT

The present invention relates to a method for the permanent reshaping and in particular straightening of keratinous fibers, in particular human keratinous fibers, such as the hair, comprising a stage of application, to the keratinous fibers, of a cosmetic composition comprising one or more non-silicone fatty substances in a content of greater than or equal to 40% by weight, with respect to the total weight of the composition, and a stage of heating the keratinous fibers using an iron, after the application of the said cosmetic composition.

20 Claims, No Drawings

METHOD FOR PERMANENT RESHAPING AND IN PARTICULAR FOR STRAIGHTENING, COMPRISING A STAGE OF STRAIGHTENING KERATINOUS FIBRES EMPLOYING A COMPOSITION COMPRISING AT LEAST 40% BY WEIGHT OF NON-SILICONE FATTY SUBSTANCES

This is a national stage application of PCT/EP2011/072585, filed internationally on Dec. 13, 2011, which claims priority to U.S. Provisional Application No. 61/434,066, filed on Jan. 19, 2011; as well as French Application FR 1060505, filed on Dec. 14, 2010.

The present invention relates to a method for the permanent reshaping and in particular straightening of keratinous fibres, in particular human keratinous fibres, such as the hair, comprising a stage of application, to the keratinous fibres, of a cosmetic composition comprising one or more non-silicone fatty substances in a content of greater than or equal to 40% by weight, with respect to the total weight of the composition, and a stage of heating the keratinous fibres using an iron, after the application of the said cosmetic composition.

Many people are not satisfied with the appearance of their hair; in particular, people who have curly hair often wish to obtain straight hair and, conversely, those who have straight hair wish to have curly hair.

The first of the techniques commonly used to obtain permanent reshaping of the hair consists, in a first step, in opening the —S—S-disulphide bonds of the keratin (keratocystine) using a composition comprising a suitable reducing agent (reduction stage) and then, after having rinsed the hair thus treated, generally with water, in reforming, in a second step, the said disulphide bonds by applying, to the hair, placed under tension beforehand, for example with curlers, an oxidizing composition (oxidation stage, also known as fixing stage), so as to finally give the hair the desired shape. This technique thus makes it possible to carry out the waving (permanent-wave method) and/or the straightening (relaxing) of the hair. The new shape imposed on the hair by chemical treatment as above is long-lasting and withstands in particular the action of washing with water or with shampoos, in contrast to simple conventional techniques for temporary reshaping, such as hair setting.

The reducing compositions which can be used for the implementation of the first stage of a permanent reshaping and in particular of a straightening generally comprise, as reducing agents, sulphites, bisulphites, alkylphosphines or, preferably, thiols. Among the latter, those commonly used are cysteine and various derivatives thereof, cysteamine and derivatives thereof, thiolactic acid or thioglycolic acid, and salts thereof and also esters thereof, especially glyceryl thioglycolate.

The oxidizing compositions required for performing the fixing step are usually compositions based on aqueous hydrogen peroxide solution.

In the context of hair relaxing and straightening techniques, this permanent reshaping operation is generally performed on curly or voluminous hair so as to obtain more or less pronounced straightening and a reduction in the volume and apparent mass of the hair.

However, such a technique is still not entirely satisfactory. This is because, although this technique proves to be very effective in modifying the shape of the hair, it still remains damaging to the hair fibres, which is mainly due to the high contents of reducing agents used in the reducing compositions and to the various, more or less lengthy, leave-in times which may occur during such a method.

This technique can thus bring about, in the long term, a detrimental change in the quality of the hair, resulting in a decline in its cosmetic properties, such as its gloss, and a deterioration in its mechanical properties, more particularly in its mechanical strength, due to swelling of the individual hairs during the rinsing between the reduction stage and the oxidation stage, which may also be reflected by an increase in the porosity of the individual hairs. These disadvantages are observed in particular with thioglycolic acid, which is generally used in a basic medium at pH values of between 8.5 and 9.5.

Moreover, if the technique of permanent reshaping of the hair described previously is applied to hair that has undergone a prior artificial coloration, it usually leads to degradation or stripping of this artificial coloration.

Similarly, if a coloration is applied to permanent-waved hair according to the technique described previously, the colour obtained is very different from the colour normally obtained on non-permanent-waved natural hair.

It has also been observed that the use of reducing agents results in an unsatisfactory durability for the straightening of the hair, in particular for the relaxing or defrizzing of the hair.

Finally, it is very often necessary to deal with problems of odours, both with the reducing compositions used, in particular those comprising thiols, and with the reduced hair.

The second of the techniques normally used to obtain hair straightening or defrizzing consists in carrying out an "lanthionization" operation using a composition comprising a base belonging to the family of the hydroxides. It results in the replacement of the disulphide (—CH$_2$—S—S—CH$_2$—) bonds by lanthionine (—CH$_2$—S—CH$_2$—) bonds. This lanthionization operation involves two consecutive chemical reactions:

The first reaction consists of a β-elimination on the cystine brought about by a hydroxide ion, resulting in the cleavage of this bond and in the formation of dehydroalanine, as represented in the following reaction scheme.

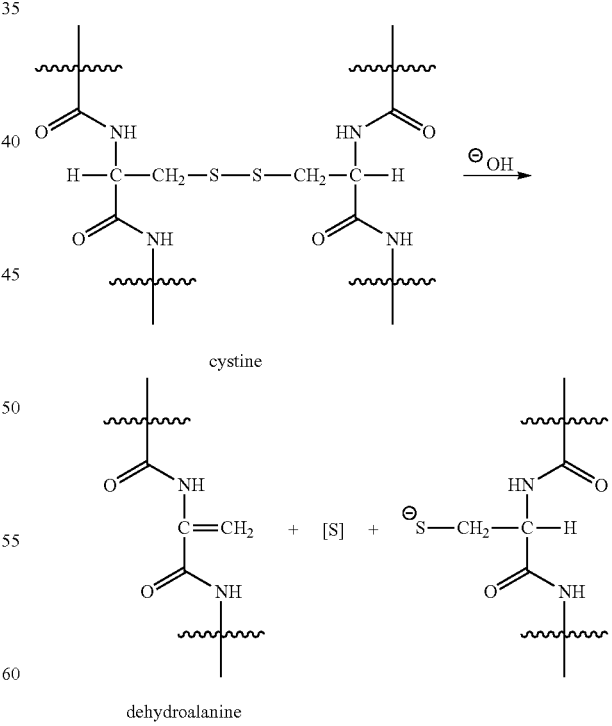

The second reaction is a reaction of the dehydroalanine with a thiol group. This is because the double bond of the dehydroalanine formed is a reactive double bond. It can react with the thiol group of the cysteine residue which was released, in order to form a new bond referred to as lanthionine bridge or bond or residue. This second reaction is illustrated by the following reaction scheme.

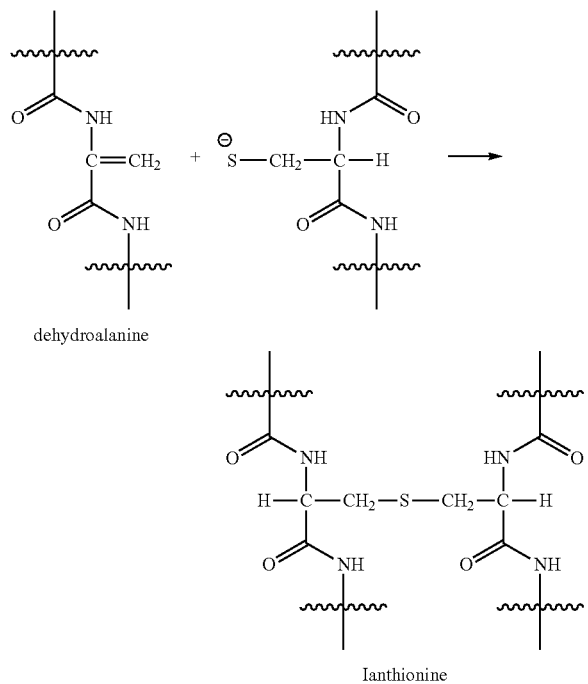

dehydroalanine lanthionine

In comparison with the first technique described above employing a reducing agent, this lanthionization technique does not require a fixing stage since the formation of the lanthionine bridge is irreversible. It is thus carried out in a single stage and makes it possible without distinction to produce either waving of the hair or the shaping or defrizzing or straightening thereof. This technique is mainly used for the shaping of naturally frizzy hair.

However, the hydroxides employed during this method exhibit the major disadvantage of being caustic. This causticity affects the scalp, causing irritation, sometimes severe irritation, and can also affect the state of the hair by rendering it, on the one hand, harsh to the touch and, on the other hand, much more fragile. The use of hydroxides can also cause, in some cases, bleaching of the natural colour of the hair.

There thus exists a real need to employ methods for the permanent reshaping and in particular the straightening of keratinous fibres, in particular human keratinous fibres, such as the hair, which do not exhibit the set of disadvantages described above, that is to say which do not involve the use of reducing agents or of alkaline agents and which make it possible to straighten keratinous fibres in a lasting way while conferring satisfactory cosmetic properties.

The Applicant Company has discovered, surprisingly, that it is possible to achieve the desired properties by employing a method for the permanent reshaping and in particular straightening or relaxing of keratinous fibres, in particular human keratinous fibres, such as the hair, comprising a stage of application, to the said keratinous fibres, of a cosmetic composition comprising one or more non-silicone fatty substances in a content of greater than or equal to 40% by weight, with respect to the total weight of the composition, and a stage of heating the said keratinous fibres at a temperature varying from 60 to 250° C. using an iron, the said stage occurring after the application of the said cosmetic composition.

The treatment method according to the invention makes it possible in particular to render the hair straight both to the touch and visually, this being achieved in a lasting fashion, while conferring good cosmetic properties on it.

In particular, the treatment method according to the invention confers, on the hair, a reshaping and in particular a straightening which is persistent with regard to shampooing operations, and also satisfactory cosmetic properties.

More particularly in the case of a straightening, it is observed that initially curly hair is straight, indeed even completely straight, after having been treated by the method according to the invention and that it remains straight even after the application of several shampooing operations.

In the same way, it is observed that hair initially very tightly curled loses its curliness after having been treated by the method according to the invention.

It has also been found that the treatment method according to the invention makes it possible to confer a more lasting straightness than a conventional care product, it being possible, for example, for the straightness to be still observed after approximately twenty shampooing operations.

Furthermore, in comparison with conventional permanent reshaping methods, the treatment method according to the invention does not require the use of a reducing composition or of a composition based on alkaline active agents and can be carried out on keratinous fibres which may be damaged, this being the case without bringing about a deterioration in the cosmetic properties or their colours.

The treatment method according to the invention also makes it possible to confer, on the hair, satisfactory cosmetic properties, in particular cosmetic properties which are satisfactory in terms of softness, feel and disentangling.

In the case of a straightening, the treatment method according to the invention also results in a reduction in the volume and in the apparent mass of the hair.

A subject-matter of the present invention is thus in particular a method for the permanent reshaping of keratinous fibres, in particular human keratinous fibres, such as the hair, comprising:

a) a stage of application, to the keratinous fibres, of a cosmetic composition comprising one or more non-silicone fatty substances in a content of greater than or equal to 40% by weight, with respect to the total weight of the said composition, and b) a stage of heating the keratinous fibres at a temperature varying from 60 to 250° C. using an iron, after application of the said composition.

The permanent reshaping is preferably a straightening of the hair.

Other subject-matters, characteristics, aspects and advantages of the invention will become even more clearly apparent on reading the description and examples which follow.

As indicated above, the cosmetic composition according to the invention comprises one or more non-silicone fatty substances in a content of greater than or equal to 40% by weight, with respect to the total weight of the composition.

The term "fatty substance" is understood to mean an organic compound which is insoluble in water at standard ambient temperature (25° C.) and at atmospheric pressure (760 mmHg), having a solubility in water of less than 5%, preferably of less than 1% and more preferably still of less than 0.1%. Non-silicone fatty substances generally exhibit, in their structure, a hydrocarbon chain comprising at least 6 carbon atoms. In addition, fatty substances are generally soluble in organic solvents under the same temperature and pressure conditions, for instance chloroform, ethanol, benzene, liquid petrolatum or decamethylcyclopentasiloxane.

The fatty substance or substances of the invention is or are furthermore nonpolyoxyethylenated and nonpolyglycerolated.

The term "non-silicone fatty substance" is understood to mean a fatty substance having a structure which does not comprise more than one silicon atom.

The fatty substance or substances can be liquid or non-liquid at ambient temperature and at atmospheric pressure.

The liquid fatty substances of the invention preferably exhibit a viscosity of less than or equal to 2 Pa·s, better still of less than or equal to 1 Pa·s and even better still of less than or equal to 0.1 Pa·s, at the temperature 25° C. and at a shear rate of $1\ s^{-1}$.

The non-silicone fatty substance or substances used in the cosmetic composition according to the invention are chosen in particular from hydrocarbons, fatty alcohols, fatty acid and/or fatty alcohol esters, nonsalified fatty acids and their mixtures.

The term "liquid hydrocarbon" means a hydrocarbon composed solely of carbon and hydrogen atoms, which is liquid at standard temperature (25° C.) and at atmospheric pressure (760 mmHg, i.e. $1.013 \times 10^5$ Pa).

More particularly, the liquid hydrocarbons are chosen from:
- linear or branched and optionally cyclic $C_6$-$C_{16}$ alkanes. Examples that may be mentioned include hexane, undecane, dodecane, tridecane and isoparaffins, for instance isohexadecane, isododecane and isodecane,
- linear or branched hydrocarbons, of mineral, animal or synthetic origin, of more than 16 carbon atoms, such as liquid paraffins and their derivatives, petrolatum, liquid petrolatum, polydecenes, hydrogenated polyisobutene, such as that sold under the Parleam® trademark by NOF Corporation, or squalane.

Preferably, the liquid hydrocarbon or hydrocarbons is or are chosen from liquid paraffins, isoparaffins, liquid petrolatum, undecane, tridecane, isododecane and their mixtures.

In a preferred alternative form, the liquid hydrocarbon or hydrocarbons is or are chosen from liquid petrolatum, isoparaffins, isododecane or a mixture of undecane and tridecane.

The term "liquid fatty alcohol" is understood to mean a nonglycerolyated and nonoxyalkylenated fatty alcohol which is liquid at standard temperature (25° C.) and at atmospheric pressure (760 mmHg, i.e. $1.013 \times 10^5$ Pa).

Preferably, the liquid fatty alcohols of the invention comprise from 8 to 30 carbon atoms.

The liquid fatty alcohols of the invention may be saturated or unsaturated.

The saturated liquid fatty alcohols are preferably branched. They may optionally comprise in their structure at least one aromatic or non-aromatic ring. They are preferably acyclic.

More particularly, the liquid saturated fatty alcohols of the invention are chosen from octyldodecanol, isostearyl alcohol and 2-hexyldecanol.

Octyldodecanol is very particularly preferred.

The liquid unsaturated fatty alcohols contain in their structure at least one double or triple bond, and preferably one or more double bonds. When several double bonds are present, there are preferably 2 or 3 of them, and they may be conjugated or nonconjugated.

These unsaturated fatty alcohols may be linear or branched.

They may optionally comprise in their structure at least one aromatic or non-aromatic ring. They are preferably acyclic.

More particularly, the liquid unsaturated fatty alcohols of the invention are chosen from oleyl alcohol, linoleyl alcohol, linolenyl alcohol and undecylenyl alcohol.

Oleyl alcohol is very particularly preferred.

The term "liquid fatty esters" is understood to mean an ester resulting from a fatty acid and/or a fatty alcohol and which is liquid at standard temperature (25° C.) and at atmospheric pressure (760 mmHg, i.e. $1.013 \cdot 10^5$ Pa).

The esters are preferably liquid esters of saturated or unsaturated and linear or branched aliphatic $C_1$-$C_{26}$ mono- or polyacids and of saturated or unsaturated and linear or branched $C_1$-$C_{26}$ aliphatic mono- or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

It is preferable, among the abovementioned esters, to use ethyl palmitate, isopropyl palmitate, myristyl palmitate, cetyl palmitate, stearyl palmitate, 2-ethylhexyl palmitate, 2-octyldecyl palmitate, alkyl myristates, such as isopropyl myristate, butyl myristate, cetyl myristate or 2-octyldodecyl myristate, hexyl stearate, propane glycol dicaprylate, butyl stearate, isobutyl stearate, dioctyl malate, hexyl laurate, 2-hexyldecyl laurate, isononyl isononanoate or cetyl octanoate.

The composition can also comprise, as liquid fatty ester, esters and diesters of sugars and of $C_6$-$C_{30}$, preferably $C_{12}$-$C_{22}$, fatty acids. It is recalled that the term "sugar" means oxygen-bearing hydrocarbon compounds containing several alcohol functional groups, with or without aldehyde or ketone functional groups, and which comprise at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, especially alkyl derivatives, such as methyl derivatives, for instance methylglucose.

The esters of sugars and of fatty acids can be chosen in particular from the group consisting of the esters or mixtures of esters of sugars described above and of saturated or unsaturated and linear or branched $C_6$-$C_{30}$, preferably $C_{12}$-$C_{22}$, fatty acids. If they are unsaturated, these compounds can comprise from one to three conjugated or nonconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates and arachidonates, or mixtures thereof, such as, in particular, oleate/palmitate, oleate/stearate or palmitate/stearate mixed esters.

More particularly, use is made of monoesters and diesters and in particular mono- or dioleates, -stearates, -behenates, -oleate/palmitates, -linoleates, -linolenates or -oleate/stearates of sucrose, glucose or methylglucose.

An example that may be mentioned is the product sold under the name Glucate® DO by Amerchol, which is a methylglucose dioleate.

Use may also be made, among the sugar esters, of pentaerythrityl esters, preferably pentaerythrityl tetraisostearate, pentaerythrityl tetraoctanoate or hexaesters of caprylic and capric acids as a mixture with dipentaerythritol.

Finally, use may also be made of natural or synthetic esters of mono-, di- or triacids with glycerol.

Among these, mention may be made of vegetable oils.

As oils of vegetable origin or synthetic triglycerides that may be used in the composition of the invention as liquid fatty esters, examples that may be mentioned include:

triglyceride oils of vegetable or synthetic origin, such as liquid triglycerides of fatty acids comprising from 6 to 30 carbon atoms, such as triglycerides of heptanoic acid or octanoic acid or also, for example, sesame, soybean, coffee, safflower, borage, sunflower, olive, apricot kernel, camellia, bambara groundnut, avocado, mango, rice bran, cottonseed, rose, kiwi seed, seabuckthorn pulp, bilberry, poppy, orange seed, sweet almond, palm, coconut, vernonia, marjoram, baobab, rapeseed, ximenia or pracaxi oil, triglycerides of caprylic/capric acids, such as those sold by Stearineries Dubois or those sold under the names Miglyol® 810, 812 and 818 by Dynamit Nobel, jojoba oil or shea butter oil.

Use will preferably be made, as liquid esters according to the invention, of triglycerides of vegetable origin, in particular the oils chosen from avocado oil, olive oil, camellia oil, apricot kernel oil, and their mixtures, and the esters of $C_4$-$C_{22}$ di- or tricarboxylic acids and of $C_1$-$C_{22}$ alcohols, in particular 1,3-propanediol dicaprylate.

In order to be regarded as a fatty substance, the fatty acid has to be in the form of a soap which is generally soluble, that is to say must not be salified by a base.

The liquid fatty acids can be chosen from acids of formula RCOOH, where R is a saturated or unsaturated and linear or branched radical preferably comprising from 7 to 39 carbon atoms.

Preferably, R is a $C_7$-$C_{29}$ alkyl or $C_7$-$C_{29}$ alkenyl group and better still a $C_{12}$-$C_{24}$ alkyl or $C_{12}$-$C_{24}$ alkenyl group. R may be substituted with one or more hydroxyl groups and/or one or more carboxyl groups.

The liquid fatty acid can be chosen in particular from oleic acid, linoleic acid and isostearic acid.

Preferably, the liquid fatty substance or substances is or are chosen from $C_6$-$C_{16}$ alkanes which are linear or branched, fatty alcohols and fatty acid esters, in particular oils of vegetable origin and esters of $C_4$-$C_{22}$ di- or tricarboxylic acids and of $C_1$-$C_{22}$ alcohols.

The fatty substance or substances used in the composition according to the invention can also be fatty substances which are non-liquid at ambient temperature (25° C.) and at atmospheric pressure (760 mmHg, i.e. $1.013 \times 10^5$ Pa).

The term "non-liquid" is preferably understood to mean a solid compound or a compound exhibiting a viscosity of greater than 2 Pa·s at the temperature of 25° C. and at a shear rate of 1 $s^{-1}$.

More particularly, the non-liquid fatty substances are chosen from fatty alcohols, fatty acid and/or fatty alcohol esters, non-silicone waxes and fatty ethers, which are non-liquid and preferably solid.

The non-liquid fatty alcohols that are suitable for use in the invention are more particularly chosen from saturated or unsaturated and linear or branched alcohols comprising from 8 to 30 carbon atoms. Mention may be made, for example, of cetyl alcohol, stearyl alcohol and a mixture thereof (cetylstearyl alcohol). Use will more particularly be made of cetylstearyl alcohol.

As regards the non-liquid fatty acid and/or fatty alcohol esters, mention may in particular be made of the solid esters resulting from $C_9$-$C_{26}$ fatty acids and from $C_9$-$C_{26}$ fatty alcohols.

Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The non-silicone wax(es) is or are chosen especially from carnauba wax, candelilla wax, esparto wax, paraffin wax, ozokerite, vegetable waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina), and ceramides.

Mention may be made, as solid amides, of ceramides. Ceramides or ceramide analogues, such as the glycoceramides which may be used in the compositions according to the invention, are known per se and are natural or synthetic molecules which can correspond to the following general formula (I):

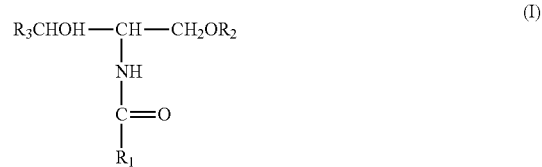

in which:
$R_1$ denotes a saturated or unsaturated and linear or branched, alkyl radical, derived from $C_{14}$-$C_{30}$ fatty acids, this radical possibly being substituted with a hydroxyl group in the α position or a hydroxyl group in the ω position esterified with a saturated or unsaturated $C_{16}$-$C_{30}$ fatty acid;
$R_2$ denotes a hydrogen atom or a (glycosyl)$_n$, (galactosyl)$_m$ or sulfogalactosyl radical, in which n is an integer ranging from 1 to 4 and m is an integer ranging from 1 to 8;
$R_3$ denotes a $C_{15}$-$C_{26}$ hydrocarbon radical which is saturated or unsaturated in the α position, this radical possibly being substituted with one or more $C_1$-$C_{14}$ alkyl radicals;
it being understood that, in the case of natural ceramides or glycoceramides, $R_3$ can also denote a $C_{15}$-$C_{26}$ α-hydroxyalkyl radical, the hydroxyl group optionally being esterified by a $C_{16}$-$C_{30}$ α-hydroxy acid.

The ceramides that are preferred in the context of the present invention are those described by Downing in Arch. Dermatol., Vol. 123, 1381-1384, 1987, or those described in French Patent FR 2 673 179.

The ceramide or ceramides which is or are more particularly preferred according to the invention is or are the compounds in which $R_1$ denotes a saturated or unsaturated alkyl derived from $C_{16}$-$C_{22}$ fatty acids, $R_2$ denotes a hydrogen atom and $R_3$ denotes a saturated linear $C_{15}$ radical.

Such compounds are, for example:
N-linoleoyldihydrosphingosine,
N-oleyldihydrosphingosine,
N-palmitoyldihydrosphingosine,
N-stearoyldihydrosphingosine,
N-behenoyldihydrosphingosine,
or mixtures of these compounds.

Even more preferentially, use is made of ceramides for which $R_1$ denotes a saturated or unsaturated alkyl radical derived from fatty acids; $R_2$ denotes a galactosyl or sulfogalactosyl radical; and $R_3$ denotes a group —CH=CH—$(CH_2)_{12}$—$CH_3$.

Other waxes or waxy starting materials that may be used according to the invention are especially marine waxes such as those sold by Sophim under the reference M82, and waxes of polyethylene or of polyolefins in general.

The non-liquid fatty ethers are chosen from dialkyl ethers and especially dicetyl ether and distearyl ether, alone or as a mixture.

Preferably, the non-silicone fatty substance or substances used in the cosmetic composition according to the invention is or are liquid at ambient temperature and at atmospheric pressure.

Preferably, the fatty substance or substances used in the cosmetic composition according to the invention is or are chosen from hydrocarbons, in particular linear or branched $C_6$-$C_{16}$ alkanes, and fatty acid esters, in particular oils of vegetable origin and esters of $C_4$-$C_{22}$ di- or tricarboxylic acids and of $C_1$-$C_{22}$ alcohols, liquid fatty alcohols and more preferably from triglycerides of vegetable origin.

More preferably still, the non-silicone fatty substance or substances is or are chosen from liquid petrolatum, isoparaffins, isododecane, undecane, tridecane, avocado oil, olive oil, camellia oil, apricot kernel oil, 1,3-propanediol dicaprylate and their mixtures.

The non-silicone fatty substance or substances used in the cosmetic composition according to the invention can be present in a content ranging from 40 to 100% by weight, preferably in a content ranging from 50 to 100% by weight and more preferably still in a content ranging from 75 to 100% by weight, with respect to the total weight of the composition.

The cosmetic composition according to the invention can be provided in particular in the form of a gel, cream, paste, foam, spray, lotion or liquid.

In particular, the cosmetic composition according to the invention can be provided in the form of an emulsion, in particular an oil-in-water (O/W), water-in-oil (W/O) or multiple (W/O/W or polyol/O/W or O/W/O) emulsion, a microemulsion or a nanoemulsion.

The cosmetic composition can additionally comprise one or more surfactants.

The surfactants optionally present in the cosmetic composition used according to the invention are in particular as follows:

The term "anionic surface-active agent" is understood to mean a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $O_2PO_2H$, $O_2PO_2H^-$ and $O_2PO_2^{2-}$.

The anionic surface-active agent or agents which can be used in the compositions of the invention is or are chosen in particular from alkyl sulphates, alkyl ether sulphates, alkylamido ether sulphates, alkylaryl polyether sulphates, monoglyceride sulphates, alkyl-sulphonates, alkylamidesulphonates, alkylarylsulphonates, α-olefinsulphonates, paraffinsulphonates, alkylsulphosuccinates, alkyl ether sulphosuccinates, alkylamide sulphosuccinates, alkyl sulphoacetates, acylsarcosinates, acylglutamates, alkyl sulphosuccinamates, acylisethionates and N-acyltaurates, polyglycoside-polycarboxylic acid and alkyl monoester salts, acyl lactylates, salts of D-galactosideuronic acids, salts of alkyl ether carboxylic acids, salts of alkylaryl ether carboxylic acids, salts of alkylamido ether carboxylic acids; or the nonsalified forms of all these compounds, the alkyl and acyl groups of all these compounds comprising from 6 to 24 carbon atoms and the aryl group denoting a phenyl group.

Some of these compounds may be oxyethylenated and then preferably comprise from 1 to 50 ethylene oxide units.

The salts of $C_{6-24}$ alkyl monoesters of polyglycoside-polycarboxylic acids may be chosen from $C_{6-24}$ alkyl polyglycoside-citrates, $C_{6-24}$ alkyl polyglycoside-tartrates and $C_{6-24}$ alkyl polyglycoside-sulphosuccinates.

When the anionic surface-active agent or agents is or are in the salt form, it is or they are not in the form of zinc salts and it/they can be chosen from salts of alkali metals, such as the sodium or potassium salt and preferably the sodium salt, salts of ammonium, salts of amines and in particular amino alcohols, and salts of alkaline earth metals, such as the magnesium salt.

Examples of aminoalcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline earth metal salts, and in particular sodium or magnesium salts, are preferably used.

Use is preferably made of ($C_{6-24}$)alkyl sulphates, ($C_{6-24}$) alkyl ether sulphates, which are optionally oxyethylenated, comprising from 2 to 50 ethylene oxide units, and their mixtures, in particular in the form of alkali metal or alkaline earth metal, ammonium or aminoalcohol salts. More preferentially, the anionic surface-acting agent or agents is or are chosen from ($C_{10-20}$)alkyl ether sulphates, and in particular sodium lauryl ether sulphate containing 2.2 mol of ethylene oxide.

When they are present, the amount of the anionic surface-active agent or agents varies preferably from 0.1% to 20% by weight, more preferably from 4% to 15% by weight, relative to the total weight of the composition.

Examples of nonionic surface-active agents that may be used in the cosmetic composition used according to the invention are described, for example, in the *Handbook of Surfactants* by M. R. Porter, published by Blackie & Son (Glasgow and London), 1991, pp. 116-178. They are chosen in particular from alcohols, α-diols or ($C_{1-20}$)alkylphenols, these compounds being polyethoxylated, polypropoxylated and/or polyglycerolated and having at least one fatty chain comprising, for example, from 8 to 18 carbon atoms, it being possible for the number of ethylene oxide and/or propylene oxide groups to range in particular from 2 to 50 and it being possible for the number of glycerol groups to range in particular from 2 to 30.

Mention may also be made of copolymers of ethylene oxide and of propylene oxide, polyoxyalkylenated fatty acid esters, optionally oxyalkylenated alkylpolyglycosides, alkylglucoside esters, N-alkylglucamine and N-acylmethylglucamine derivatives, aldobionamides and amine oxides.

Unless otherwise mentioned, "fatty" compound (for example a fatty acid) denotes, for these surfactants, a compound comprising, in its main chain, at least one saturated or unsaturated alkyl chain comprising at least 6 carbon atoms, preferably from 8 to 30 carbon atoms and better still from 10 to 22 carbon atoms.

When they are present, the amount of the nonionic surface-active agent or agents varies preferably from 0.01% to 20% by weight, more preferably from 0.2% to 10% by weight, relative to the total weight of the composition.

The amphoteric or zwitterionic surface-active agent or agents that may be used in the present invention may especially be derivatives of optionally quaternized aliphatic secondary or tertiary amine, in which the aliphatic group is a linear or branched chain containing from 8 to 22 carbon atoms, the said amine derivatives containing at least one anionic group such as, for example, a carboxylate, sulphonate, sulphate, phosphate or phosphonate group. Mention may in particular be made of ($C_8$-$C_{20}$)alkyl betaines, sulphobetaines, ($C_8$-$C_{20}$ alkyl)amido($C_{3-8}$ alkyl)betaines or ($C_8$-$C_{20}$ alkyl)amido($C_6$-$C_8$ alkyl)sulphobetaines. Mention may also be made, among the derivatives of optionally quaternized aliphatic secondary or tertiary amines as defined above which can be used, of the compounds with the following respective structures (II) and (III):

Ra-CONHCH$_2$CH$_2$—N$^+$(Rb)(Rc)(CH$_2$COO$^-$)     (II)

in which:
Ra represents a $C_{10}$-$C_{30}$ alkyl or alkenyl group derived from an acid
Ra-COOH, preferably present in hydrolysed coconut oil, represents a heptyl, nonyl or undecyl group,
Rb represents a β-hydroxyethyl group, and
Rc represents a carboxymethyl group;
and

Ra'-CONHCH$_2$CH$_2$—N(B)(B')     (III)

in which:
B represents —CH$_2$CH$_2$OX',
B' represents —(CH$_2$)$_z$—Y', with z=1 or 2,
X' represents the group —CH$_2$—COOH, CH$_2$—COOZ', —CH$_2$CH$_2$—COOH, —CH$_2$CH$_2$—COOZ', or a hydrogen atom,
Y' represents —COOH, —COOZ' or the group —CH$_2$—CHOH—SO$_3$H or —CH$_2$—CHOH—SO$_3$Z',
Z' represents an ion derived from an alkali metal or alkaline earth metal, such as sodium, an ammonium ion or an ion derived from an organic amine,
Ra' represents a $C_{10}$-$C_{30}$ alkyl or alkenyl group of an acid Ra'-COOH preferably present in hydrolysed linseed oil or coconut oil, an alkyl group, in particular a $C_{17}$ alkyl group and its iso form, or an unsaturated $C_{17}$ group.

These compounds are classified in the CTFA dictionary, 5th edition, 1993, under the names disodium cocoamphodiacetate, di sodium lauroamphodiacetate, di sodium caprylamphodiacetate, disodium capryloamphodiacetate, disodium cocoamphodipropionate, di sodium lauroamphodipropionate, di sodium caprylamphodipropionate, disodium caryloamphodipropionate, lauroamphodipropionic acid and cocoamphodipropionic acid.

By way of example, mention may be made of the cocoamphodiacetate sold by Rhodia under the trade name Miranol® C2M Concentrate.

Among the abovementioned amphoteric or zwitterionic surface-active agents, it is preferred to use ($C_8$-$C_{20}$ alkyl) betaines such as cocoyl betaine, and ($C_8$-$C_{20}$ alkyl)amido($C_2$-$C_8$ alkyl) betaines such as cocoylamidopropyl betaine, and mixtures thereof. More preferably, the amphoteric or zwitterionic surface-active agent or agents is or are chosen from cocoylamidopropyl betaine and cocoyl betaine.

When they are present, the amount of the amphoteric or zwitterionic surface-active agent or agents is preferably in the range from 0.01% to 20% by weight, more preferably from 0.5% to 10% by weight, relative to the total weight of the composition.

The term "cationic surfactant" means a surfactant that is positively charged when it is contained in the composition according to the invention. This surface-active agent can carry one or more permanent positive charges or can comprise one or more functional groups which can be converted to cations within the composition according to the invention.

The cationic surfactant or surfactants is or are preferably selected from primary, secondary or tertiary fatty amines, optionally polyoxyalkylenated, or salts thereof, and quaternary ammonium salts, and mixtures thereof.

The fatty amines generally comprise at least one $C_8$-$C_{30}$ hydrocarbon chain. Mention may be made, among the fatty amines which can be used according to the invention, for example, of stearylamidopropyldimethylamine and distearylamine.

Examples of quaternary ammonium salts that may especially be mentioned include:
those corresponding to the general formula (IV) below:

$$\left[ \begin{array}{cc} R_8 & R_{10} \\ \diagdown & \diagup \\ & N \\ \diagup & \diagdown \\ R_9 & R_{11} \end{array} \right]^+ X^-$$
    (IV)

in which the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ denoting a group containing from 8 to 30 carbon atoms, preferably from 12 to 24 carbon atoms. The aliphatic groups can comprise heteroatoms, such as, in particular, oxygen, nitrogen, sulphur and halogens. The aliphatic groups are, for example, chosen from $C_{1-30}$ alkyl, $C_{1-30}$ alkoxy, polyoxy($C_2$-$C_6$)alkyl ene, $C_{1-30}$ alkylamide, ($C_{12}$-$C_{22}$)alkylamido-($C_2$-$C_6$)alkyl, ($C_{12}$-$C_{22}$)alkyl acetate and $C_{1-30}$ hydroxyalkyl groups; X$^-$ is an anion chosen from the group of the halides, phosphates, acetates, lactates, ($C_1$-$C_4$)alkyl sulphates, ($C_1$-$C_4$)alkylsulphonates or ($C_1$-$C_4$)-alkylarylsulphonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by Van Dyk. It is particularly preferred to use the chloride salts of these compounds;

quaternary ammonium salts of imidazoline, such as, for example, those of formula (V) below:

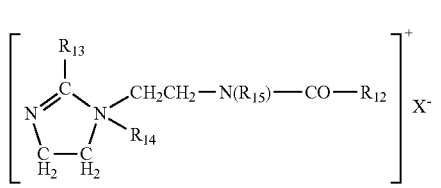

in which $R_{12}$ represents an alkenyl or alkyl group comprising from 8 to 30 carbon atoms, for example derived from tallow fatty acids, $R_{13}$ represents a hydrogen atom, a $C_1$-$C_4$ alkyl group or an alkenyl or alkyl group comprising from 8 to 30 carbon atoms, $R_{14}$ represents a $C_1$-$C_4$ alkyl group, $R_{15}$ represents a hydrogen atom or a $C_1$-$C_4$ alkyl group and $X^-$ is an anion chosen from the group of the halogens, phosphates, acetates, lactates, alkyl sulphates, alkylsulphonates or alkylarylsulphonates, the alkyl and aryl groups of which preferably comprise, respectively, from 1 to 20 carbon atoms and from 6 to 30 carbon atoms. $R_{12}$ and $R_{13}$ preferably denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by Rewo;

quaternary diammonium or triammonium salts, in particular of formula (VI):

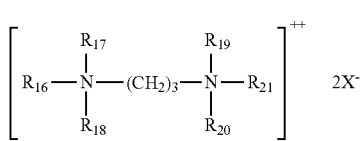

in which $R_{16}$ denotes an alkyl radical containing approximately from 16 to 30 carbon atoms, which is optionally hydroxylated and/or interrupted with one or more oxygen atoms, $R_{17}$ is chosen from hydrogen or an alkyl radical containing from 1 to 4 carbon atoms or a group $(R_{16a})(R_{17a})(R_{18a})N-(CH_2)_3$, $R_{16a}$, $R_{17a}$, $R_{18a}$, $R_{18}$, $R_{19}$, $R_{20}$ and $R_{21}$, which may be identical or different, are chosen from hydrogen or an alkyl radical containing from 1 to 4 carbon atoms, and $X^-$ is an anion chosen from the group of halides, acetates, phosphates, nitrates and methyl sulphates. Compounds of this kind are, for example, Finquat CT-P, available from Finetex (Quaternium 89), and Finquat CT, available from Finetex (Quaternium 75), quaternary ammonium salts containing at least one ester functional group, such as those of formula (VII) below:

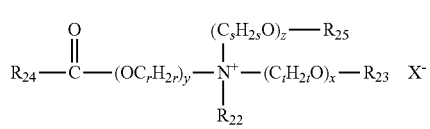

in which:
$R_{22}$ is chosen from $C_1$-$C_6$ alkyl groups and $C_1$-$C_6$ hydroxyalkyl or dihydroxyalkyl groups;

$R_{23}$ is selected from:
the group

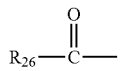

$R_{27}$ groups, which are saturated or unsaturated and linear or branched $C_1$-$C_{22}$ hydrocarbon groups,
the hydrogen atom,
$R_{25}$ is chosen from:
the group

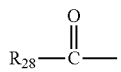

$R_{29}$ groups, which are saturated or unsaturated and linear or branched $C_1$-$C_6$ hydrocarbon groups,
the hydrogen atom,
$R_{24}$, $R_{26}$ and $R_{28}$, which are identical or different, are chosen from saturated or unsaturated and linear or branched $C_7$-$C_{21}$ hydrocarbon groups;
r, s and t, which may be identical or different, are integers ranging from 2 to 6;
$r_1$ and $t_1$, which are identical or different, have the value 0 or 1,
and $r_2+r_1=2r$ and $t_1+t_2=2t$,
y is an integer having a value from 1 to 10;
x and z, which may be identical or different, are integers ranging from 0 to 10;
$X^-$ is a simple or complex and organic or inorganic anion;
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ can be linear or branched and more particularly linear.

Preferably, $R_{22}$ denotes a methyl, ethyl, hydroxyethyl or dihydroxypropyl group and more particularly a methyl or ethyl group.

Advantageously, the sum x+y+z has a value from 1 to 10.

When $R_{23}$ is a hydrocarbon group $R_{27}$, it can be long and have from 12 to 22 carbon atoms or short and have from 1 to 3 carbon atoms.

When $R_{25}$ is a hydrocarbon group $R_{29}$, it preferably has from 1 to 3 carbon atoms.

Advantageously, $R_{24}$, $R_{26}$ and $R_{28}$, which are identical or different, are chosen from saturated or unsaturated and linear or branched $C_{11}$-$C_{21}$ hydrocarbon groups and more particularly from saturated or unsaturated and linear or branched $C_{11}$-$C_{21}$ alkyl and alkenyl groups.

Preferably, x and z, which are identical or different, have the value 0 or 1.

Advantageously, y is equal to 1.

Preferably, r, s and t, which are identical or different, have the value 2 or 3 and more particularly still are equal to 2.

The anion $X^-$ is preferably a halide (chloride, bromide or iodide) or an alkyl sulphate, more particularly methyl sulphate. However, it is possible to use methanesulphonate, phosphate, nitrate, tosylate, an anion derived from an organic acid, such as acetate or lactate, or any other anion compatible with the ammonium comprising an ester functional group.

The anion $X^-$ is even more particularly chloride or methyl sulphate.

Use is made more particularly, in the composition according to the invention, of the ammonium salts of formula (VII) in which:

$R_{22}$ denotes a methyl or ethyl group,
x and y are equal to 1;
z is equal to 0 or 1;
r, s and t are equal to 2;
$R_{23}$ is selected from:
the group

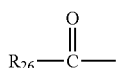

methyl, ethyl or $C_{14}$-$C_{22}$ hydrocarbon groups,
the hydrogen atom;
$R_{25}$ is chosen from:
the group

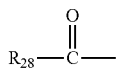

the hydrogen atom;
$R_{24}$, $R_{26}$ and $R_{28}$, which are identical or different, are chosen from saturated or unsaturated and linear or branched $C_{13}$-$C_{17}$ hydrocarbon groups and preferably from saturated or unsaturated and linear or branched $C_{13}$-$C_{17}$ alkyl and alkenyl groups.

The hydrocarbon groups are advantageously linear.

Mention may be made, for example, of the compounds of formula (VI), such as diacyloxyethyldimethylammonium, diacyloxyethyl(hydroxyethyl)methylammonium, monoacyloxyethyldi(hydroxyethyl)methylammonium, triacyloxyethylmethylammonium and monoacyloxyethyl(hydroxyethyl)dimethylammonium salts (in particular chloride or methyl sulphate) and their mixtures. The acyl groups preferably contain 14 to 18 carbon atoms and are obtained more particularly from a vegetable oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with $C_{10}$-$C_{30}$ fatty acids or with mixtures of $C_{10}$-$C_{30}$ fatty acids of vegetable or animal origin, or by transesterification of their methyl esters. This esterification is followed by a quaternization using an alkylating agent, such as an alkyl halide (preferably methyl halide or ethyl halide), a dialkyl sulphate (preferably dimethylsulphate or diethylsulphate), methyl methanesulphonate, methyl paratoluenesulphonate, glycol chlorohydrin or glycerol chlorohydrin.

Such compounds are sold, for example, under the names Dehyquart® by Henkel, Stepanquat® by Stepan, Noxamium® by Ceca or Rewoquat® WE 18 by Rewo-Witco.

The composition according to the invention can comprise, for example, a mixture of quaternary ammonium mono-, di- and triester salts, with a predominance by weight of diester salts.

It is also possible to use the ammonium salts containing at least one ester functional group that are described in U.S. Pat. No. 4,874,554 and U.S. Pat. No. 4,137,180.

Use may be made of behenoylhydroxypropyltrimethylammonium chloride, provided by Kao under the name Quatarmin BTC 131.

Preferably, the ammonium salts containing at least one ester functional group contain two ester functional groups.

Among the quaternary ammonium salts containing at least one ester functional group which may be used, it is preferred to use dipalmitoylethylhydroxyethylmethylammonium salts.

When they are present, the amount of the cationic surface-active agent or agents is preferably in the range from 0.01% to 20% by weight and better still from 0.5% to 10% by weight, relative to the total weight of the composition.

Preferably, the cosmetic composition according to the invention comprises one or more nonionic surfactants chosen in particular from polyoxyethylenated ($C_{1-20}$)alkylphenols, such as beheneth-10.

The cosmetic composition according to the invention can additionally comprise one or more thickening agents.

Within the meaning of the present invention, the term "thickening agent" is understood to mean an agent which, introduced at 1% by weight into an aqueous solution or aqueous/alcoholic solution comprising 30% of ethanol and at pH=7 or into an oil chosen from liquid petrolatum, isopropyl myristate or cyclopentadimethylsiloxane, makes it possible to achieve a viscosity of at least 100 cPs, preferably at least 500 cPs, at 25° C. and at a shear rate of 1 $s^{-1}$. This viscosity may be measured using a cone/plate viscometer (Haake R600 rheometer or the like).

The thickening agent or agents possibly present in the cosmetic composition according to the invention can be chosen from cellulose thickening agents, for example hydroxyethylcellulose, hydroxypropylcellulose and carboxymethylcellulose, guar gum and its derivatives, for example hydroxypropyl guar, sold by Rhodia under the reference Jaguar HP 105, gums of microbial origin, such as xanthan gum and scleroglucan gum, synthetic thickening agents, such as crosslinked homopolymers of acrylic acid or of acrylamidopropane-sulphonic acid, for example Carbomer, or nonionic, anionic, cationic or amphoteric associative polymers, such as the polymers sold under the names Pemulen TR1 or TR2 by Goodrich, Salcare SC90 by Ciba, Aculyn 22, 28, 33, 44 or 46 by Rohm & Haas and Elfacos T210 and T212 by Akzo. Mention may also be made of thickening polymers of polysaccharide type.

Preferably, the cosmetic composition according to the invention comprises one or more nonionic thickening agents, in particular one or more cellulose thickening agents and especially xanthan gum.

According to one embodiment, the cosmetic composition comprises one or more fatty substances, in a content of at least 40% by weight, chosen from triglycerides of vegetable origin and one or more nonionic thickening agents.

According to one embodiment, the cosmetic composition comprises one or more non-silicone fatty substances, in a content of at least 40% by weight, chosen from triglycerides of vegetable origin, one or more nonionic thickening agents and one or more nonionic surfactants.

The cosmetic composition can comprise water. If the composition comprises water, its content generally varies from 5 to 60% by weight, preferably from 5 to 50% by weight and better still from 5 to 40% by weight, with respect to the total weight of the composition.

The compositions of the invention can comprise one or more volatile or non-volatile and linear, branched or cyclic silicones.

These silicones, preferably polydimethylsiloxanes, may or may not be organomodified. The term "organomodified" is understood to mean silicones carrying functional groups, such as amine, amide, hydroxyl, aryl, carboxyl, phosphate, alkoxy or polyoxyalkylene functional groups.

Preferably, the silicones are polydimethylsiloxanes which are optionally aminated and/or polyoxyethylenated.

The composition can additionally comprise one or more additives chosen from the cosmetic adjuvants and active principles commonly used in the hair field. These additives are chosen, for example, from conditioning agents, such as cationic polymers, chitosans and their derivatives, vitamins, amino acids, oligopeptides, peptides, hydrolysed or nonhydrolysed and modified or nonmodified proteins, enzymes, organic acids other than nonsalified fatty acids, UV screening agents, antioxidants and agents for combating free radicals, chelating agents, antidandruff agents, seborrhoea-regulating agents, soothing agents, hair colouring agents, such as direct dyes, oxidation dye precursors and pigments, acids, bases, plasticizers, fragrances, preservatives, inorganic fillers, pearlescent agents or glitter.

These additives are present in the composition according to the invention in an amount ranging from 0 to 20% by weight relative to the total weight of the composition.

The cosmetic composition according to the invention can be employed on dry or wet hair, preferably on wet hair, with or without a leave-in time.

After application of the cosmetic composition according to the invention and before raising the temperature of the keratinous fibres using an iron, the said composition can be left to stand for a period of time ranging from 5 to 60 minutes, preferably ranging from 5 to 15 minutes. The leave-in time can be passed under heat and in particular under an occlusive system.

The cosmetic composition according to the invention is applied to the keratinous fibres at a level of 0.1 to 10 grams, preferably of 0.2 to 5 grams, of composition per gram of keratinous fibres.

After application of the cosmetic composition according to the invention, the keratinous fibres can be wrung out in order to remove the excess composition.

As explained above, the method according to the invention comprises a stage of heating the hair at a temperature varying from 60 to 250° C., which is carried out using an iron after application of the cosmetic composition according to the invention.

The heating stage is necessary to optimize the effects of the method.

The term "iron" is understood to mean, within the meaning of the present invention, a device for heating keratinous fibres, the said fibres and the heating device being brought into contact.

The end of the iron which comes into contact with the keratinous fibres generally exhibits two flat surfaces. These two surfaces can be made of metal. In particular, these two surfaces can be smooth or crimped.

The heating stage can be carried out using a straightening iron, a curling iron, a crimping iron or a steam iron. Preferably, the heating stage is performed using a straightening iron.

Mention may be made, as example of irons which can be used in the straightening method according to the invention, of any type of flat iron and in particular, without implied limitation, of those described in U.S. Pat. No. 5,957,140 and U.S. Pat. No. 5,046,516.

The iron can be applied by successive separate strokes lasting a few seconds or by gradual movement or sliding along the locks.

Preferably, the iron is applied in the method according to the invention by a continuous movement from the root to the tip, in one or more passes, in particular in two passes each lasting from 5 seconds to 1 minute.

The use of the iron during the method according to the invention provides the keratinous fibres with a dry heat and not with a wet heat, which makes possible reshaping and in particular permanent straightening of the keratinous fibres.

Preferably, the stage of heating the hair is carried out at a temperature varying from 100 to 250° C., preferably from 190 to 220° C., better still from 200 to 215° C. and in particular at a temperature of 210° C., for a period of time which can range from 5 seconds to one hour and preferably from 5 seconds to one minute.

The straightening method according to the invention can also comprise an additional stage of predrying after the application of the cosmetic composition and before the stage of heating the keratinous fibres carried out at a temperature ranging from 60 to 250° C., so as to prevent significant releases of vapours which might burn the hands of the hairdresser and the scalp of the person. The predrying stage can be carried out using a hand-held hairdryer or a hood dryer or by drying in the open air.

After the passage of the iron, the keratinous fibres can optionally be rinsed or washed with a shampoo. The keratinous fibres are subsequently optionally dried using a hand-held hairdryer or a hood dryer.

The straightening method according to the invention advantageously does not comprise the application of a reducing composition, neither before nor during nor after the application of the cosmetic composition according to the invention.

In particular, the cosmetic composition according to the invention is preferably devoid of reducing agents.

The term "composition devoid of reducing agents" is understood to mean, within the meaning of the present invention, a composition comprising less than 1% by weight of reducing agents, with respect to the total weight of the composition, and preferably a composition not comprising reducing agents.

According to one embodiment, the permanent reshaping method and in particular straightening method according to the invention comprises a stage of application of a cosmetic composition comprising one or more non-silicone fatty substances in a content of greater than or equal to 40% by weight, with respect to the total weight of the composition, a stage of carrying out one or more cosmetic treatments of the keratinous fibres, in particular a stage of application of a shampoo to the fibres, and a stage of heating the keratinous fibres using an iron, after application of the said cosmetic composition according to the invention, this being done until the desired shape or the desired shape intensity is obtained.

When relaxing or defrizzing the hair, the cosmetic composition is applied to the hair, preferably wet hair, and then the hair is subjected to a mechanical reshaping, which makes it possible to fix it in its new shape, by an operation of straightening the hair with a wide-toothed comb, with the back of a comb, with the hand or with a brush.

The stage of heating the hair is subsequently carried out at a temperature varying from 60 to 250° C. using an iron, preferably a flat iron, as indicated above.

Preferably, the treatment method is carried out on tightly curled or curly hair.

The present invention also relates to a kit comprising a cosmetic composition comprising one or more non-silicone fatty substances in a content of greater than or equal to 40% by weight and an iron which provides a temperature varying from 60 to 250° C.

The following examples are given by way of illustration of the present invention.

EXAMPLE

I. Compositions Tested a. Compositions Comprising 100% of Oils

The compositions (A) to (F) according to the invention are prepared from the ingredients shown in the table below, the amounts of which are expressed as percent by weight, with respect to the total weight of the composition.

| Compositions | A | B | C | D | E | F |
|---|---|---|---|---|---|---|
| Avocado oil | 100 | — | — | — | — | — |
| Olive oil | — | 100 | — | — | — | — |
| Camellia oil | — | — | 100 | — | — | — |
| Apricot kernel oil | — | — | — | 100 | — | — |
| Liquid petrolatum | — | — | — | — | 100 | — |
| Isoparaffin | — | — | — | — | — | 100 | b. Compositions Comprising a Mixture of Fatty Substances

The compositions (G) to (K) according to the invention are prepared from the ingredients shown in the table below, the amounts of which are expressed as percent by weight, with respect to the total weight of the composition.

| Compositions | G | H | I | J | K |
|---|---|---|---|---|---|
| Avocado oil | 50 | — | — | — | 50 |
| Camellia oil | — | — | — | 50 | — |
| Liquid petrolatum | — | 50 | 50 | — | — |
| 1,3-Propanediol dicaprylate | 50 | 50 | — | — | 50 |
| Isododecane | — | — | 25 | 50 | — |
| Undecane/tridecane | — | — | 25 | — | — | c. Compositions Comprising an Emulsified Oil

The compositions (L) and (M) according to the invention are prepared from the ingredients shown in the table below, the amounts of which are expressed as percent by weight, with respect to the total weight of the composition.

| Compositions | L | M |
|---|---|---|
| Avocado oil | 50 | 55 |
| Cetylstearyl alcohol | 5 | — |
| Beheneth-10 | 10 | 10 |
| Xanthan gum | — | 0.5 |
| Water | 35 | 39.5 |

II. Application to Locks

1. Application Protocol

Locks of natural tightly curled hair weighing 2.7 grams are washed beforehand with a shampoo.

2.7 grams of each of the compositions (A) to (M) or the reference composition 1 (water) are applied to each of the locks. After a leave-in time of 10 minutes, the locks are subsequently wrung out, to remove the excess product, and then they are predried with a hand-held hairdryer at a temperature of 60° C.

A straightening iron is subsequently applied at a temperature of 210° C., two passes being carried out. The locks are washed with a shampoo and are then dried.

A panel of experts compares the effects introduced by the compositions (A) to (M) according to the invention and the reference composition 1 comprising only water.

2. Results

It is observed that the locks treated with the compositions (A) to (M) according to the invention are visually straight.

It is also found that, after three shampooing operations, the locks treated with the compositions (A) to (M) are still straight and exhibit good cosmetic properties. This straightening is persistent after ten shampooing operations.

It is found that the locks treated with the reference composition 1 regain their original curliness from the time of the shampooing carried out at the end of the application protocol.

III. Application to Heads

1. Model with Curly Hair—Composition (A)/Reference Composition 1 Comparison a. Application Protocol 12 grams of the composition (A) according to the invention and 12 grams of the reference composition 1 (water) are applied to each half-head of a model having curly hair, and the compositions are left to stand for 10 minutes. After the leave-in time, the hair is subsequently wrung out, to remove the excess product, and then the hair is predried using a hang-held hairdryer at a temperature of 60° C.

A straightening iron is subsequently applied at a temperature of 210° C., two passes being carried out. The hair of the model is subsequently washed with a shampoo and is then dried.

A panel of experts compares the effects introduced into the hair by the compositions (A) and 1.

b. Results

It is found that the hair treated with the composition (A) is completely straight, whereas the hair treated with the composition 1 regains its initial curls after the shampooing which is carried out at the end of the application protocol.

It is also found that, after twenty-three shampooing operations, the hair treated with the composition (A) is still straight.

2. Model with Tightly Curled Hair—Composition (A)/Reference Composition 1 Comparison a. Application Protocol 12 grams of the composition (A) according to the invention and 12 grams of the reference composition 1 are applied to each half-head of a model having very tightly curled hair, and the compositions are left to stand for 10 minutes. After the leave-in time, the hair is subsequently wrung out, to remove the excess product, and then the hair is predried using a hang-held hairdryer at a temperature of 60° C.

A straightening iron is subsequently applied at a temperature of 210° C., two passes being carried out. The locks are subsequently washed with a shampoo and are then dried.

b. Results

It is found that the hair treated with the composition (A) changes from the very tightly curled state to the slightly curly state, whereas the hair treated with the composition 1 regains its initial curliness after the shampooing which is carried out at the end of the application protocol.

It is also found that, after twelve shampooing operations, the hair treated with the composition (A) is still relaxed.

3. Model with Curly Hair—Composition (C)/Reference Composition 1 Comparison a. Application Protocol The procedure employed is identical to that described in Point 1.a.

b. Results

It is found that the hair treated with the composition (C) is straight, whereas the hair treated with the reference composition 1 regains its initial curls after the shampooing which is carried out at the end of the application protocol.

It is also found that, after eighteen shampooing operations, the hair treated with the composition (C) is still straight.

The invention claimed is:

1. A method for the permanent reshaping of keratinous fibers comprising steps of:
    applying to the keratinous fibers a cosmetic composition comprising at least one non-silicone fatty substance in an amount of greater than or equal to about 40% by weight, with respect to the total weight of the cosmetic composition, and
    heating the keratinous fibers at a temperature ranging from about 60° C. to about 250° C. using an iron.

2. The method according to claim 1, wherein the at least one non-silicone fatty substance is chosen from is liquids and non-liquids at ambient temperature and at atmospheric pressure.

3. The method according to claim 2, wherein the at least one non-silicone fatty substance is a liquid non-silicone fatty substance chosen from hydrocarbons, fatty alcohols, fatty acid esters, fatty alcohol esters, and fatty acids.

4. The method according to claim 2, wherein the at least one non-silicone fatty substance is a liquid non-silicone fatty substance chosen from hydrocarbons, fatty alcohols, and fatty acid esters.

5. The method according to claim 2, wherein the at least one non-silicone fatty substance is a non-liquid fatty substance chosen from fatty alcohols, fatty acid esters, fatty alcohol esters, non-silicone waxes, and fatty ethers.

6. The method according to claim 5, wherein the at least one non-liquid fatty substance is a fatty alcohol chosen from saturated and unsaturated and linear and branched alcohols comprising from 8 to 30 carbon atoms.

7. The method according to claim 1, wherein the at least one non-silicone fatty substance is chosen from liquid petrolatum, isoparaffins, isodedecane, undecane, tridecane, avocado oil, olive oil, camellia oil, apricot kernel oil, and 1,3-propanediol dicaprylate.

8. The method according to claim 1, wherein the cosmetic composition further comprises at least one surfactant.

9. The method according to claim 8, wherein the at least one surfactant is a nonionic surfactant.

10. The method according to claim 1, wherein the cosmetic composition further comprises at least one thickening agent.

11. The method according to claim 10, wherein the at least one thickening agent is a nonionic thickening agent.

12. The method according to claim 1, wherein the at least one non-silicone fatty substance is present in the cosmetic composition in an amount ranging from about 40% to about 100% by weight, with respect to the total weight of the composition.

13. The method according to claim 1, wherein the at least one non-silicone fatty substance is present in the cosmetic composition in an amount ranging from about 75% to about 100% by weight, with respect to the total weight of the composition.

14. The method according to claim 1, wherein the temperature ranges from about 100° C. to about 250° C.

15. The method according to claim 1, wherein the temperature ranges from about 200° C. to about 215° C.

16. The method according to claim 1, further comprising a step of pre-drying the keratinous fibers before the step of heating the keratinous fibers.

17. The method according to claim 1, wherein the composition comprises water in an amount ranging from about 5% to about 60% by weight, with respect to the total weight of the composition.

18. The method according to claim 1, wherein the composition comprises water in an amount ranging from about 5% to about 40% by weight, with respect to the total weight of the composition.

19. A method for straightening hair, comprising steps of:
    applying to the hair a cosmetic composition comprising at least one non-silicone fatty substance in an amount of greater than or equal to about 40% by weight, with respect to the total weight of the cosmetic composition, and
    heating the hair at a temperature ranging from about 60° C. to about 250° C. using an iron.

20. A kit comprising:
    a cosmetic composition comprising at least one non-silicone fatty substance in an amount of greater than or equal to about 40% by weight, and
    an iron that is capable of providing a temperature ranging from about 60° C. to about 250° C.

* * * * *